United States Patent
Johnston et al.

(10) Patent No.: US 9,179,231 B2
(45) Date of Patent: Nov. 3, 2015

(54) SYSTEMS AND METHODS FOR FACILITATING TIME-BASED FITTING BY A SOUND PROCESSOR

(75) Inventors: Jacob Johnston, Moorpark, CA (US); Guillermo A. Calle, Moorpark, CA (US); Fernando Chapa, Quartz Hill, CA (US)

(73) Assignee: Advanced Bionics AG, Staefa (CH)

( * ) Notice: Subject to any disclaimer, the term of this patent is extended or adjusted under 35 U.S.C. 154(b) by 27 days.

(21) Appl. No.: 14/114,909

(22) PCT Filed: May 31, 2011

(86) PCT No.: PCT/US2011/038508
§ 371 (c)(1),
(2), (4) Date: Oct. 30, 2013

(87) PCT Pub. No.: WO2012/166108
PCT Pub. Date: Dec. 6, 2012

(65) Prior Publication Data
US 2014/0086439 A1   Mar. 27, 2014

(51) Int. Cl.
 H04R 29/00  (2006.01)
 H04R 25/00  (2006.01)
 A61N 1/36   (2006.01)
 A61N 1/372  (2006.01)
(52) U.S. Cl.
 CPC ............ H04R 25/70 (2013.01); A61N 1/36032 (2013.01); A61N 1/37235 (2013.01)
(58) Field of Classification Search
 CPC ..................................................... H04R 25/70
 USPC ...................................................... 381/60, 314
 See application file for complete search history.

(56) References Cited

U.S. PATENT DOCUMENTS

| 8,644,535 | B2 | 2/2014 | Steinbuss |
| 2006/0210103 | A1 | 9/2006 | Van den Heuvel |
| 2007/0156063 | A1* | 7/2007 | Zoth et al. ..................... 600/559 |
| 2009/0154743 | A1 | 6/2009 | Lundh et al. |
| 2011/0087085 | A1 | 4/2011 | Tsampazis et al. |
| 2011/0194706 | A1* | 8/2011 | Shim ................................ 381/60 |
| 2011/0249838 | A1* | 10/2011 | Neumeyer et al. ............ 381/314 |
| 2011/0249839 | A1* | 10/2011 | Mindlin et al. ............... 381/314 |

FOREIGN PATENT DOCUMENTS

DE   19542961   5/1997

OTHER PUBLICATIONS

International Search Report and Written Opinion received in International Application No. PCT/US2011/038508 dated Feb. 21, 2012.

\* cited by examiner

*Primary Examiner* — Davetta W Goins
*Assistant Examiner* — Amir Etesam
(74) *Attorney, Agent, or Firm* — ALG Intellectual Property, LLC

(57) ABSTRACT

An exemplary sound processor (104) included in an auditory prosthesis system includes 1) a clock facility (406) configured to detect an elapsing of a predetermined amount of time and 2) a fitting facility (408) communicatively coupled to the clock facility and configured to automatically perform, in response to the elapsing of the predetermined amount of time, one or more fitting operations with respect to the auditory prosthesis system. Corresponding systems and methods are also disclosed.

19 Claims, 12 Drawing Sheets

US 9,179,231 B2

SYSTEMS AND METHODS FOR FACILITATING TIME-BASED FITTING BY A SOUND PROCESSOR

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to stimulation sites (e.g., auditory nerve fibers) by way of one or more channels formed by an array of electrodes implanted in an auditory prosthesis patient. Direct stimulation of the stimulation sites leads to the perception of sound in the brain and at least partial restoration of hearing function.

When an auditory prosthesis (e.g., a cochlear implant) is initially implanted in a patient, and during follow-up tests and checkups thereafter, it is usually necessary to fit the auditory prosthesis system to the patient. These fitting sessions are typically performed under the supervision of an audiologist or the like at a clinic. Unfortunately, this requires the patient to make repeated trips to the clinic, which can be costly, time-consuming, and inconvenient for both the patient and the audiologist. While some clinical visits involve a great deal of patient-clinician interaction, other clinical visits are very routine and follow strict processes.

SUMMARY

An exemplary sound processor included in an auditory prosthesis system includes 1) a clock facility configured to detect an elapsing of a predetermined amount of time and 2) a fitting facility communicatively coupled to the clock facility and configured to automatically perform, in response to the elapsing of the predetermined amount of time, one or more fitting operations with respect to the auditory prosthesis system.

An exemplary system includes 1) a fitting facility configured to perform an initial fitting operation with respect to an auditory prosthesis system used by a patient while a sound processor included in the auditory prosthesis system is communicatively coupled to the system, 2) a user interface facility communicatively coupled to the fitting facility and configured to receive user input representative of an amount of time and a subsequent fitting operation to be performed by the sound processor with respect to the auditory prosthesis system in response to an elapsing of the amount of time, and 3) and a programming facility communicatively coupled to the user interface facility and configured to program the sound processor to automatically perform the subsequent fitting operation in response to an elapsing of the amount of time.

An exemplary method includes 1) detecting, by a sound processor included in an auditory prosthesis system, an elapsing of a predetermined amount of time and 2) automatically performing, by the sound processor in response to the elapsing of the predetermined amount of time, one or more fitting operations with respect to the auditory prosthesis system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
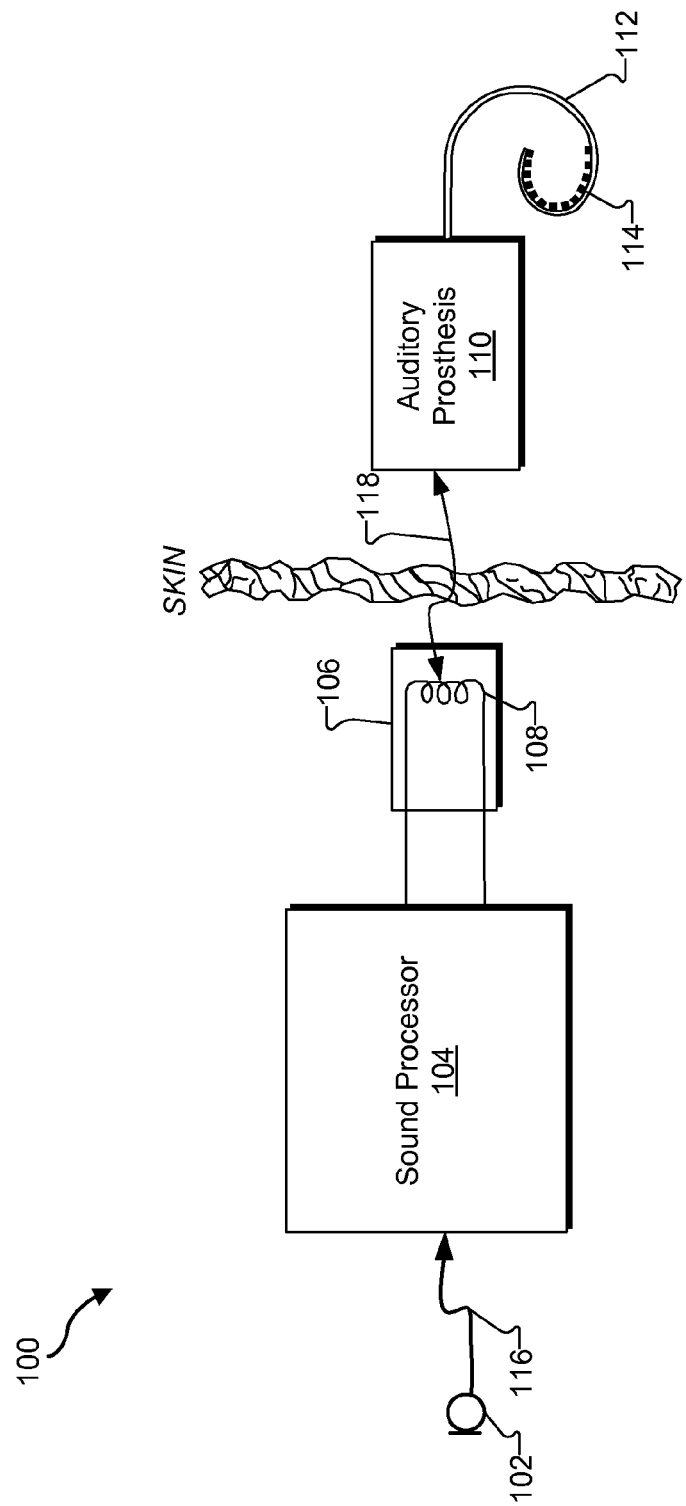
FIG. 1 illustrates an exemplary auditory prosthesis system according to principles described herein.

Systems and methods for facilitating time-based fitting by a sound processor included in an auditory prosthesis system are described herein. As will be described in more detail below, the systems and methods described herein may obviate the need for an auditory prosthesis patient to visit a clinic so that various fitting operations associated with his or her auditory prosthesis system may be performed. This may make the fitting process associated with an auditory prosthesis system easier, less costly, more reliable, and more convenient for both the patient and the clinician.

To illustrate, during an initial fitting session at a clinic, a sound processor may be programmed to subsequently (e.g., after the patient has left the clinic) perform one or more fitting operations after a predetermined time period has elapsed. For example, a sound processor may be programmed to automatically switch from operating in accordance with a particular sound processing program to operating in accordance with a different sound processing program after a predetermined number of days following a visit to the clinic by the patient. Additionally or alternatively, the sound processor may periodically (e.g., every fifteen days) perform one or more measurements (e.g., electrode impedance measurements, electrical field imaging ("EFI") measurements, and/or neural response imaging ("NRI") measurements) and adjust one or more control parameters associated with a sound processing program that governs an operation of the sound processor in accordance with the one or more measurements. Follow-up support may be provided for any of these fitting operations by telephone, email, or in any other manner.

Numerous advantages and benefits other than those described above are associated with the systems and methods described herein. For example, overall performance of an auditory prosthesis system may be increased due to the automatic and periodic nature of the fitting operations described herein. For example, each electrode implanted within an auditory prosthesis patient has a certain impedance associated therewith. These impedance values are often used to determine one or more optimal control parameters associated with a particular sound processing program. However, electrode impedances may fluctuate and/or change over time as a result of illness, diet, medications, and other factors. Without compensating adjustments being made to the sound processing program, these fluctuations and changes in electrode impedance may result in decreased sound quality, distorted pitch, and/or system malfunction. As will be described in more detail below, the systems and methods described herein may automatically recognize and remedy such changes in electrode impedance without the patient having to visit a clinic.

As used herein, the term "sound processing program" refers to any program that is executable by a sound processor included in an auditory prosthesis system. Hence, a sound processing program may specify a particular mode in which the sound processor is to operate. For example, a sound processing program may define a set of control parameters selected to optimize a listening experience of an auditory prosthesis patient in a particular listening environment (e.g., a relatively quiet room, a noisy restaurant, a musical environment, etc.).

To facilitate an understanding of the methods and systems described herein, an exemplary auditory prosthesis system 100 will be described in connection with FIG. 1. As shown in FIG. 1, auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient, and auditory prosthesis 110, lead 112, electrodes 114 may be implanted subcutaneously with the patient. In some alternative examples, microphone 102 and/or sound processor 104 may also be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing program loaded on sound processor 104 to generate appropriate stimulation parameters for controlling auditory prosthesis 110. In certain examples, sound processor may 104 may include multiple sound processing programs loaded thereon such that a patient may select, from the multiple sound processing programs, which sound processing program to utilize to generate stimulation parameters. Accordingly, the patient may select a sound processing program that is well suited for a particular situation.

Sound processor 104 may include or be implemented by a behind-the-ear ("BTE") unit, an off-the-ear speech processor (i.e., a speech processor configured to be worn off the ear, such as a portable speech processor ("PSP")), and/or any other sound processing unit as may serve a particular implementation. Exemplary components of sound processor 104 will be described in more detail below.

Sound processor 104 may be configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M" levels), threshold current levels ("T" levels), clipping levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more electrodes 114 disposed along lead 112. In some examples, auditory prosthesis 110 may include a plurality of independent current sources each associated with a channel defined by one or more of electrodes 114. In this manner, different stimulation current levels may be applied to multiple stimulation sites simultaneously by way of multiple electrodes 114. In such examples, auditory prosthesis system 100 may be referred to as a "multi-channel auditory prosthesis system."

To facilitate application of the electrical stimulation generated by auditory prosthesis 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
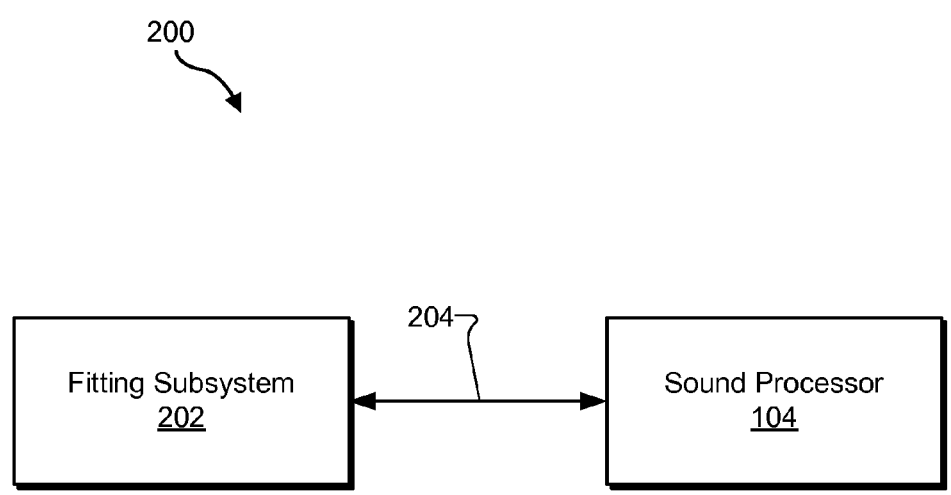
FIG. 2 illustrates an exemplary auditory prosthesis fitting system according to principles described herein.

FIG. 2 illustrates an exemplary auditory prosthesis fitting system 200 (or simply "fitting system 200") that may be used to fit auditory prosthesis system 100 to a patient. As used herein, the terms "fitting a sound processor to a patient" and "fitting an auditory prosthesis system to a patient" will be used interchangeably to refer to performing one or more fitting operations or procedures associated with sound processor 104 and/or any other component of auditory prosthesis system 100.

As shown in FIG. 2, fitting system 200 may include a fitting subsystem 202 configured to be selectively and communicatively coupled to sound processor 104 of auditory prosthesis system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting procedures and/or operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. In some examples, fitting subsystem 202 may perform one or more initial fitting operations with respect to an auditory prosthesis system to a patient. One or more subsequent fitting operations may be performed by the sound processor, as will be described in more detail below.

Figure 3:
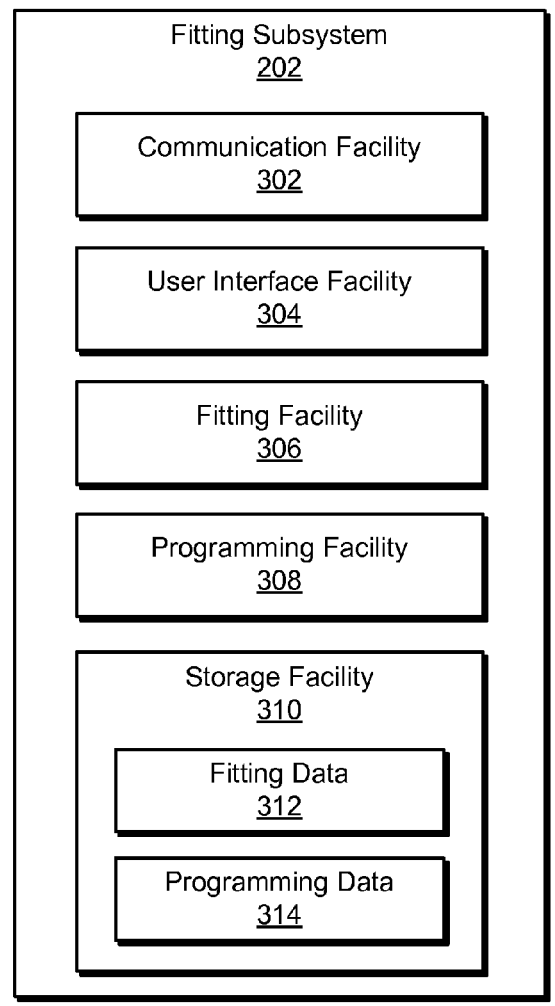
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a programming facility 306, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

In some examples (e.g., during a fitting of a bilateral auditory prosthesis patient), communication facility 302 may facilitate selective and/or concurrent communication between multiple sound processors (e.g., right and left sound processors). In this manner, communication facility 302 may be configured to communicate with a first auditory prosthesis associated with a first ear (e.g., the right ear) of the patient by way of a first sound processor and a second auditory prosthesis associated with a second ear (e.g., the left ear) of the patient by way of a second sound processor.

Communication facility 302 may additionally or alternatively be configured to facilitate communication between fitting subsystem 302 and one or more other devices. For example, communication facility 302 may be configured to facilitate communication between fitting subsystem 202 and one or more computing devices (e.g., by way of the Internet and/or one or more other types of networks).

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display.

In some examples, user interface facility 304 may be configured to receive (e.g., by way of one or more GUIs) user input representative of an amount of time (also referred to as a "time period") and one or more fitting operations to be performed by a sound processor (e.g., sound processor 104) with respect to an auditory prosthesis system (e.g., system 100) of which the sound processor is a part in response to an elapsing of the amount of time. To illustrate, user interface facility 304 may receive user input comprising instructions configured to direct the sound processor to switch from operating in accordance with a first sound processing program to operating in accordance with a second sound processing program after a particular amount of time (e.g., 30 days) has elapsed. Exemplary manners in which the user input may be received by user interface facility 304 will be described in more detail below.

Fitting facility 306 may be configured to perform one or more fitting procedures and/or operations described herein. For example, fitting facility 306 may be configured to perform an initial fitting operation when an auditory prosthesis is first implanted within a patient. To illustrate, fitting facility 306 may load a particular sound processing program onto the sound processor and direct the sound processor to operate in accordance with the sound processing program. Other fitting operations may be performed by fitting facility 306 as may serve a particular implementation. For example, fitting facility 306 may define and/or adjust one or more control parameters, direct sound processor 104 to measure one or more electrode impedances, perform one or more neural response detection operations, and/or perform one or more testing, diagnostic, and/or troubleshooting operations associated with auditory prosthesis system 100.

Programming facility 308 may be configured to program a sound processor communicatively coupled to fitting subsystem 202 to perform one or more operations as may serve a particular implementation. For example, programming facility 308 may program the sound processor to automatically perform one or more fitting operations (e.g., one or more fitting operations specified by an audiologist or other clinician and received by user interface facility 304) in response to an elapsing of a predetermined amount of time (e.g., as specified by an audiologist).

Programming facility 308 may be configured to program a sound processor in any suitable manner. For example, programming facility 308 may transmit data representative of one or more programming instructions to the sound processor by way of a CPI device.

Storage facility 308 may be configured to maintain fitting data 312 representative of or associated with one or more fitting operations performed by fitting facility 306, programming data 314 representative of or associated with one or more programming operations performed by programming facility 308, and/or any other type of data as may serve a particular implementation.

Figure 4:
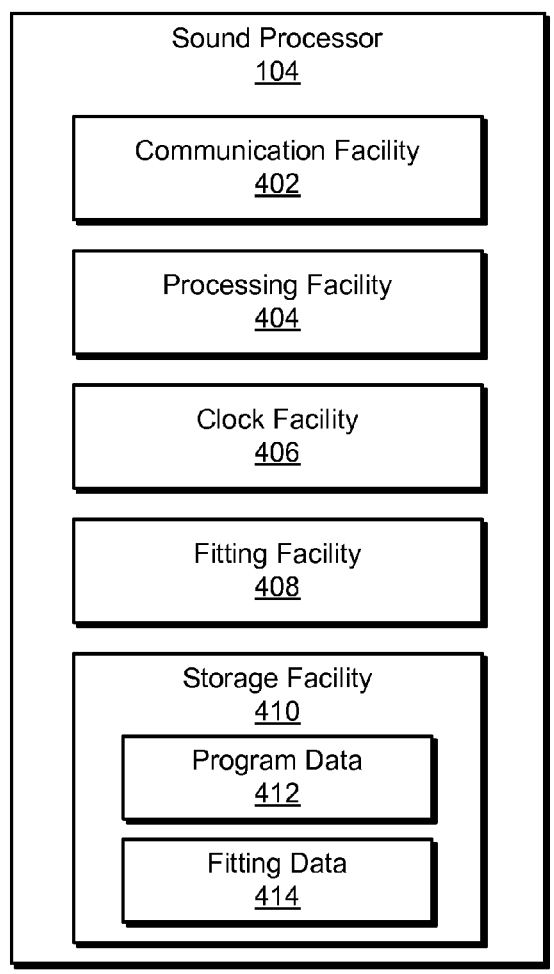
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, a clock facility 406, a fitting facility 408, and a storage facility 410, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and auditory prosthesis 110. For example, communication facility 402 may include transceiver components configured to wirelessly transmit data (e.g., control parameters and/or power signals) to auditory prosthesis 110 and/or wirelessly receive data from auditory prosthesis 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of auditory prosthesis 110 (e.g., one or more stimulation parameters defining the electrical stimulation to be generated and applied by auditory prosthesis 110). Processing facility 404 may be configured to operate in accordance with one or more sound processing programs and/or control parameters loaded onto sound processor 104 by fitting subsystem 202 and/or otherwise stored within storage facility 410.

Clock facility 406 may be configured to keep track of time and detect an elapsing of predetermined amount of time (e.g., a number of days). In some examples, clock facility 406 may be configured to detect multiple elapsing of a predetermined time period. For example, clock facility 406 may detect and notify one or more other facilities included in sound processor 104 (e.g., fitting facility 408) each time a particular time period (e.g., 15 days) elapses.

In some examples, clock facility 406 is implemented by a real-time clock that tracks actual times and dates. Alternatively, clock facility 406 may be implemented by a counter or timer. Clock facility 406 may be configured to operate even while sound processor 104 is in an off state (e.g., when sound processor 104 is not being worn by a patient).

In some examples wherein sound processor 104 does not have clock circuitry configured to operate while sound processor 104 is in an off state, clock facility 406 may be implemented by a counter or the like configured to track the occurrence of certain events associated with sound processor 104. For example, clock facility 406 may be implemented by a counter configured to track battery depletion cycles (i.e., the number of times that a battery that is a part of sound processor 104 and/or auditory prosthesis 110 is drained a certain amount (e.g., a full amount)). Based on this information, clock facility 406 may generate an estimate of elapsed time.

In some alternative embodiments, clock facility 406 may be implemented by an auditory prosthesis. For example, auditory prosthesis 110 may include a real-time clock and/or counter configured to track time and detect an elapsing of a predetermined amount of time. However, for illustrative purposes, it will be assumed that clock facility 406 is implemented by sound processor 104 in the examples provided herein.

Fitting facility 408 may be configured to perform one or more of the fitting operations described herein. For example, fitting facility 408 may automatically perform one or more fitting operations in response to an elapsing of a predetermined amount of time. To illustrate, fitting facility 408 may be configured to automatically switch from operating in accordance with a particular sound processing program to operating in accordance with a different sound processing program after a predetermined number of days following an initial fitting performed by fitting subsystem 202. The initial fitting may be performed right after an auditory prosthesis is implanted in a patient and/or during a subsequent visit by the patient to a clinic. Additionally or alternatively, fitting facility 408 may periodically (e.g., every fifteen days) perform one or more measurements (e.g., electrode impedance measurements, electrical field imaging ("EFI") measurements, and/or neural response imaging ("NRI") measurements) and adjust one or more control parameters associated with a sound processing program that governs an operation of sound processor 104 in accordance with the one or more measurements. These fitting operations will be described in more detail below.

Storage facility 410 may be configured to maintain program data 412 representative of one or more sound processing programs loaded onto sound processor 104 and fitting data 414 utilized by clock facility 406 and/or fitting facility 408. Storage facility 410 may be configured to maintain additional or alternative data as may serve a particular implementation.

Figure 5:
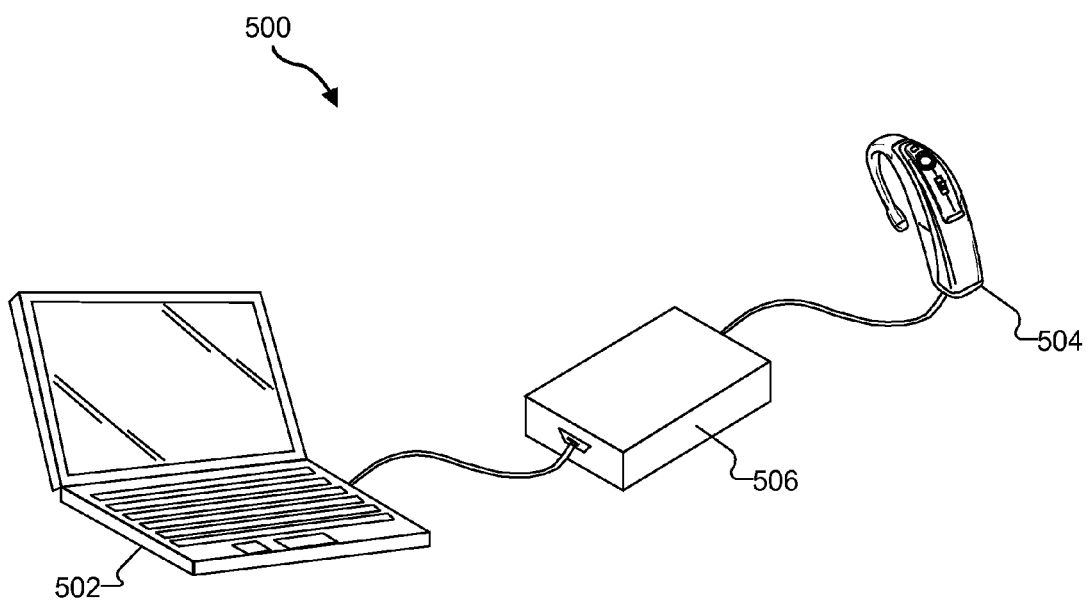
FIG. 5 illustrates an exemplary implementation of the auditory prosthesis fitting system of FIG. 2 according to principles described herein.

FIG. 5 illustrates an exemplary implementation 500 of fitting system 200. In implementation 500, a fitting station 502 may be selectively and communicatively coupled to a behind-the-ear ("BTE") sound processor 504 (or simply "sound processor 504") by way of a CPI device 506.

Fitting station 502 may include any suitable computing device and/or combination of computing devices and be configured to perform one or more of the fitting operations described herein. Fitting station 502 may be utilized by an audiologist, a clinician, and/or any other user to fit sound processor 504 to a patient.

As shown, sound processor 504 is configured to be worn behind or on the ear of a patient. However, it will be recognized that sound processor 504 may additionally or alternatively include a sound processor configured to be worn by a patient off the ear (e.g., a body worn sound processor).

CPI device 506 may be configured to facilitate communication between fitting station 502 and sound processor 504. In some examples, CPI device 506 may be selectively and communicatively coupled to fitting station 502 and/or sound processor 504 by way of one or more ports included within fitting station 502 and sound processor 504.

It will be recognized that fitting station 502 may be concurrently coupled to more than one sound processor 504. For example, fitting station 502 may be coupled to two sound processors 504 (e.g., by way of two CPI devices 506) when a bilateral auditory prosthesis patient is being fitted.

Figure 6:
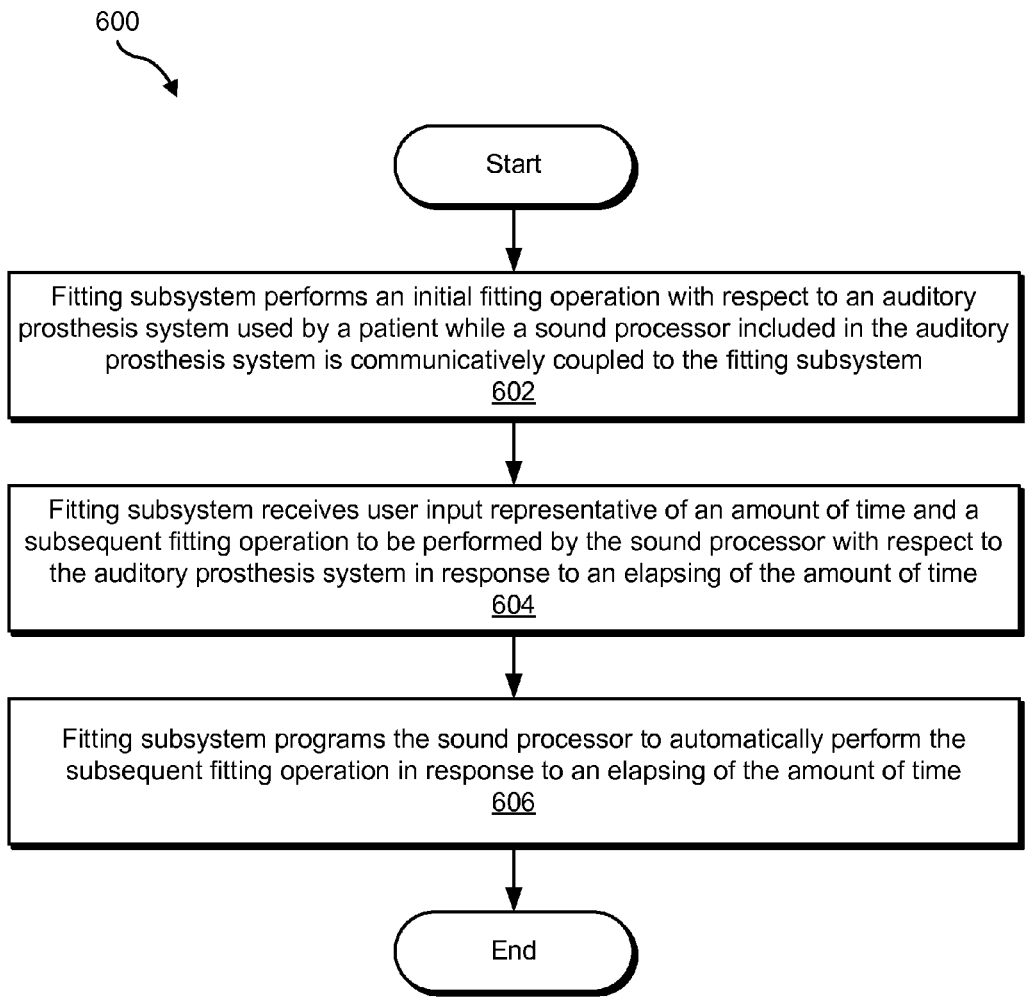
FIG. 6 illustrates an exemplary method of facilitating time-based fitting by a sound processor included in an auditory prosthesis system according to principles described herein.

FIG. 6 illustrates an exemplary method 600 of facilitating time-based fitting by a sound processor included in an auditory prosthesis system. While FIG. 6 illustrates exemplary steps according to one embodiment, other embodiments may omit, add to, reorder, combine, and/or modify any of the steps shown in FIG. 6. One or more of the steps shown in FIG. 6 may be performed by any component or combination of components of fitting subsystem 202 and/or fitting station 502.

In step 602, a fitting subsystem performs an initial fitting operation with respect to an auditory prosthesis system used by a patient while a sound processor included in the auditory prosthesis system is communicatively coupled to the fitting subsystem. Step 602 may be performed in any of the ways described herein.

In step 604, the fitting subsystem receives user input representative of an amount of time and a subsequent fitting operation to be performed by the sound processor with respect to the auditory prosthesis system in response to an elapsing of the amount of time. Step 604 may be performed in any of the ways described herein.

In step 606, the fitting subsystem programs the sound processor to automatically perform the subsequent fitting operation in response to an elapsing of the amount of time. Step 606 may be performed in any of the ways described herein.

Figure 7:
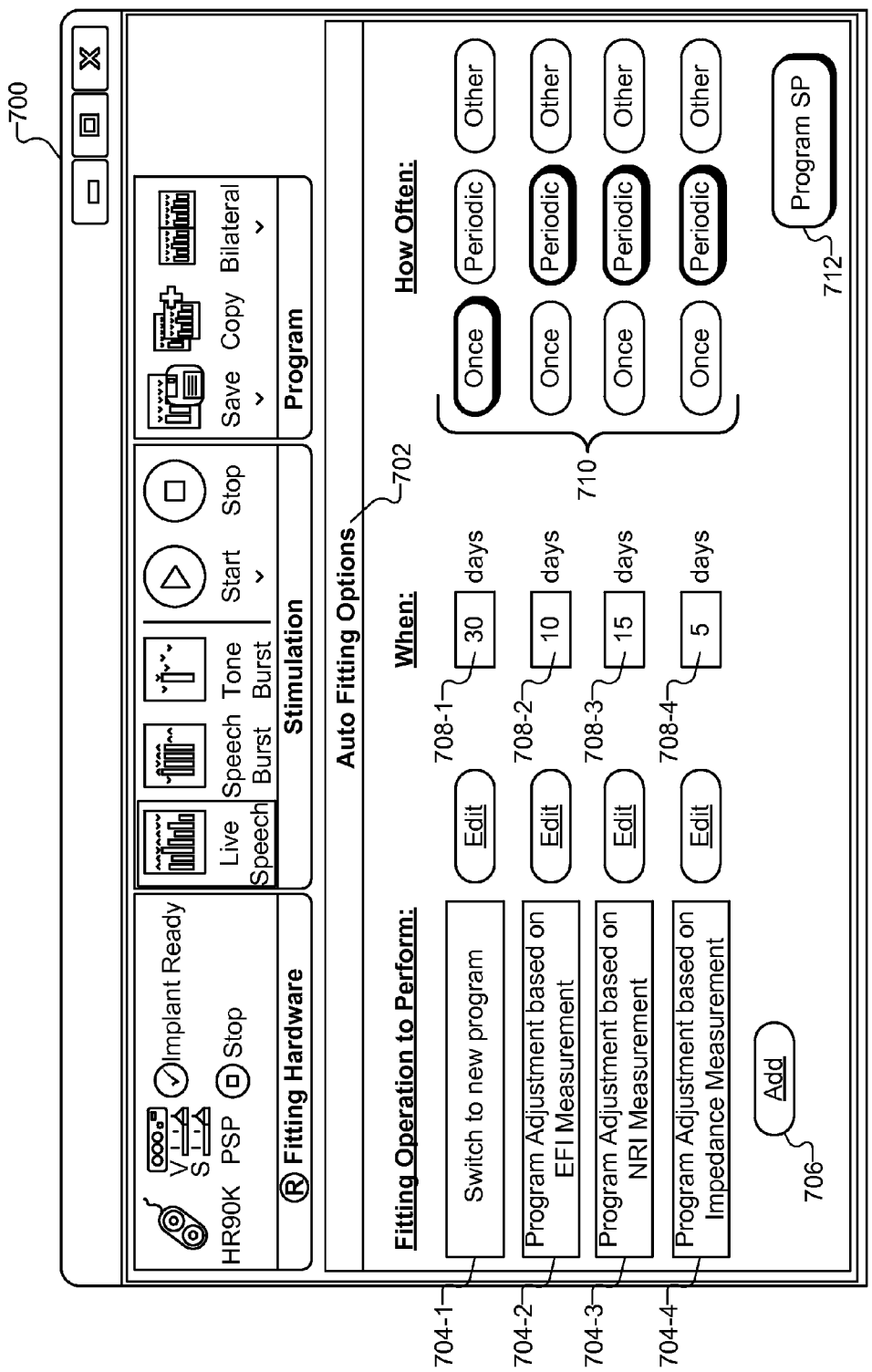
FIG. 7 shows an exemplary graphical user interface ("GUI") that may be presented by a fitting subsystem and that may be configured to facilitate programming of a sound processor to perform one or more fitting operations in response to an elapsing of one or more predetermined amounts of time according to principles described herein.

An implementation of method 600 will be described in connection with FIG. 7. FIG. 7 shows an exemplary GUI 700 that may be presented by fitting subsystem 202 and that may be configured to facilitate programming of a sound processor to perform one or more fitting operations in response to an elapsing of one or more predetermined amounts of time. It will be recognized that GUI 700 is merely illustrative of the many different GUIs that may be configured to facilitate programming of a sound processor to perform one or more fitting operations in response to an elapsing of one or more predetermined amounts of time.

As shown, GUI 700 includes a variety of "auto fitting" options 702 available to an audiologist or other user of fitting subsystem 202. A user may interact with (e.g., select, set, modify, and/or add to) the auto fitting options 702 in order to set one or more programming instructions for a sound processor communicatively coupled to fitting subsystem 202.

To illustrate, FIG. 7 shows that various fitting operations 704 (e.g., a fitting operation 704-1 entitled "switch to new program," a fitting operation 704-2 entitled "program adjustment based on EFI measurement," a fitting operation 704-3 entitled "program adjustment based on NRI measurement," and a fitting operation 704-4 entitled "program adjustment based on impedance measurement") to be performed by the sound processor after the sound processor has been disconnected from fitting subsystem 202 have been selected by a user. Additional fitting operations may be specified by selecting an "add" option 706.

As shown in FIG. 7, a user may also specify a particular amount of time that the sound processor is to wait before performing each of the fitting operations 704. For example, a user may enter a number into fields 708-1 through 708-4 (collectively referred to as "fields 708") to specify an amount of time that the sound processor is to wait before performing fitting operations 704-1 through 704-4, respectively. As shown, a user has specified that the sound processor is to wait 30 days before performing fitting operation 704-1, 10 days before performing fitting operation 704-2, 15 days before performing fitting operation 704-3, and 5 days before performing fitting operation 704-4. It will be recognized that the amount of time entered into fields 708 may be measured from (i.e., in relation to) any starting time as may serve a particular implementation. For example, the amounts of time may be measured from the time or day that the fitting operations are specified in GUI 700, from the time or day of a particular fitting procedure (e.g., an initial fitting of an auditory prosthesis system to a patient), and/or from any other time as may serve a particular implementation.

A user may also schedule how often each fitting operation 704 is to be performed by the sound processor by selecting one or more of options 710. For example, the sound processor may be programmed to perform a particular fitting operation once, on a periodic basis, or in accordance with any suitable schedule as may serve a particular implementation. For example, FIG. 7 shows that fitting operation 704-1 has been scheduled to be performed once and that fitting operations 704-2 through 704-4 have been scheduled to be performed on a periodic basis (e.g., every 10 days, every 15 days, or every 5 days).

Once the desired auto fitting options have been specified, a user may select a "program SP" option 712 to direct fitting subsystem 202 (e.g., programming facility 308) to program the sound processor with the specified auto fitting options. The sound processor may then subsequently perform the specified fitting operations 704 in accordance with the specified time periods.

Figure 8:
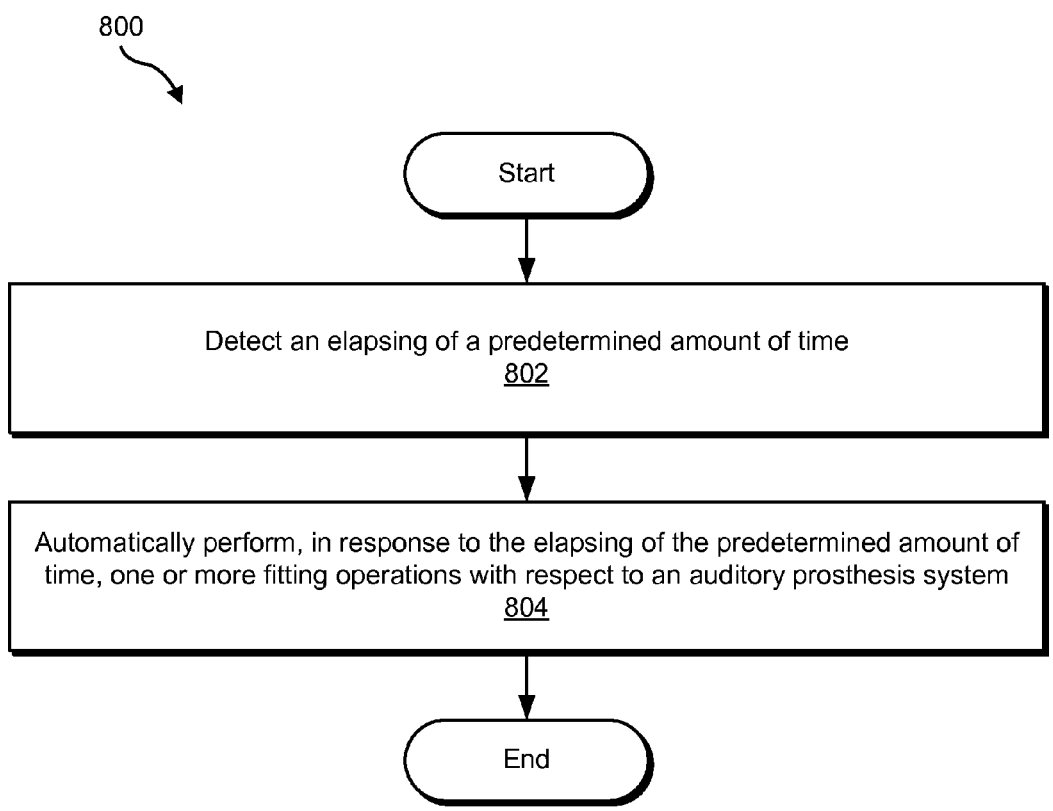
FIG. 8 illustrates another exemplary method of facilitating time-based fitting by a sound processor included in an auditory prosthesis system according to principles described herein.

FIG. 8 illustrates another exemplary method 800 of facilitating time-based fitting by a sound processor included in an auditory prosthesis system. While FIG. 8 illustrates exemplary steps according to one embodiment, other embodiments may omit, add to, reorder, combine, and/or modify any of the steps shown in FIG. 8. One or more of the steps shown in FIG. 8 may be performed by any component or combination of components of sound processor 104 and/or sound processor 504.

In step 802, a sound processor included in an auditory prosthesis system detects an elapsing of a predetermined amount of time. Step 802 may be performed in any of the ways described herein.

In step 804, the sound processor automatically performs, in response to the elapsing of the predetermined amount of time, one or more fitting operations with respect to the auditory prosthesis system. The one or more fitting operations may include any of the fitting operations described herein. Step 804 may be performed in any of the ways described herein.

Specific examples of the systems and methods described herein will now be described in connection with FIGS. 9-11. It will be recognized that the examples described in connection with FIGS. 9-11 are merely illustrative of the many different implementations of the systems and methods described herein.

Figure 9:
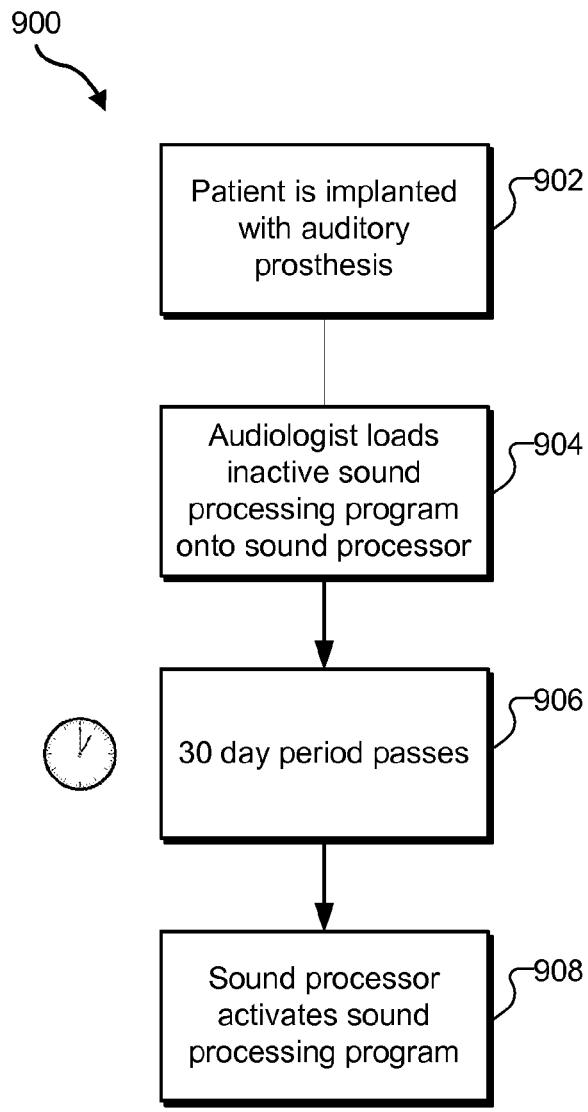
FIGS. 9-11 illustrate various examples of the systems and methods described herein.

FIG. 9 illustrates an exemplary scenario 900 in which it is desirable for a sound processor to switch to a new sound processing program after a certain number of days. For example, a patient may be implanted with an auditory prosthesis, as shown in step 902. Immediately after the auditory prosthesis is implanted, an audiologist may program a sound processor associated with the auditory prosthesis to operate in accordance with a relatively basic sound processing program so that the patient has a chance to grow accustomed to the auditory prosthesis system before a more complex sound processing program is implemented. Hence, in step 904, the audiologist may load an inactive sound processing program (i.e., the more complex sound processing program) onto the sound processor and specify particular time period (i.e., 30 days) that the sound processor must wait before activating sound processing program.

After the 30 day period passes (step 906), the sound processor may detect activate the previously inactive sound processing program (step 908) and begin operating in accordance with the sound processing program. The sound processing program may be automatically activated by the sound processor after the 30 day period has passed, thereby obviating the need for the patient to make a trip to the audiologist's clinic so that the audiologist may load the sound processing program on the sound processor.

Figure 10:
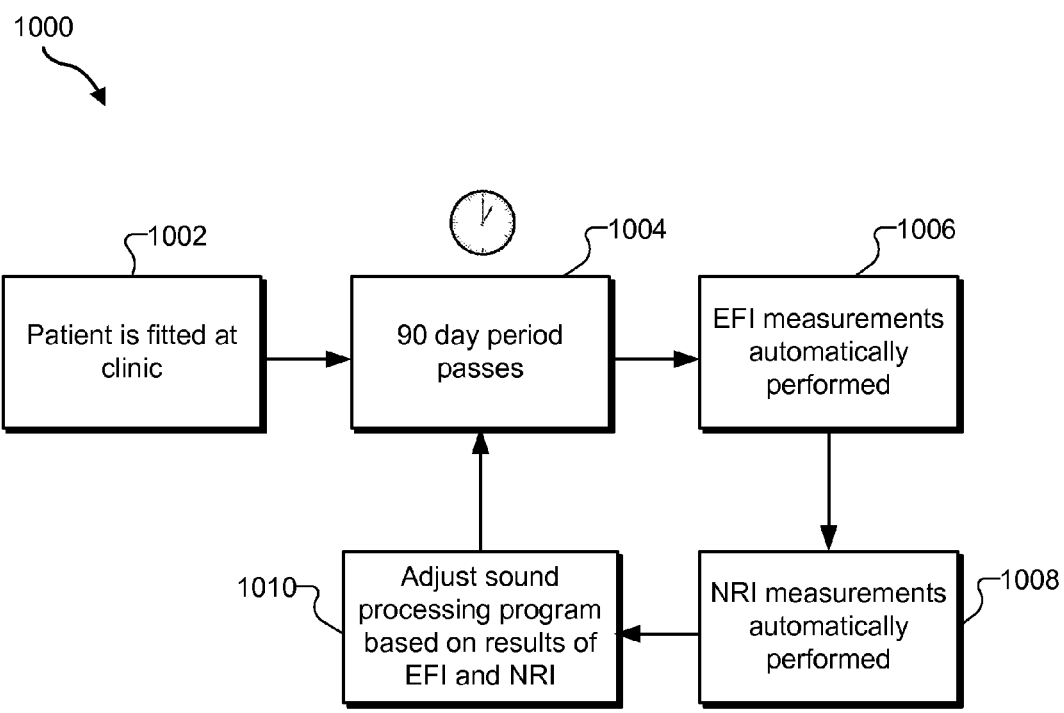
Figure 11:
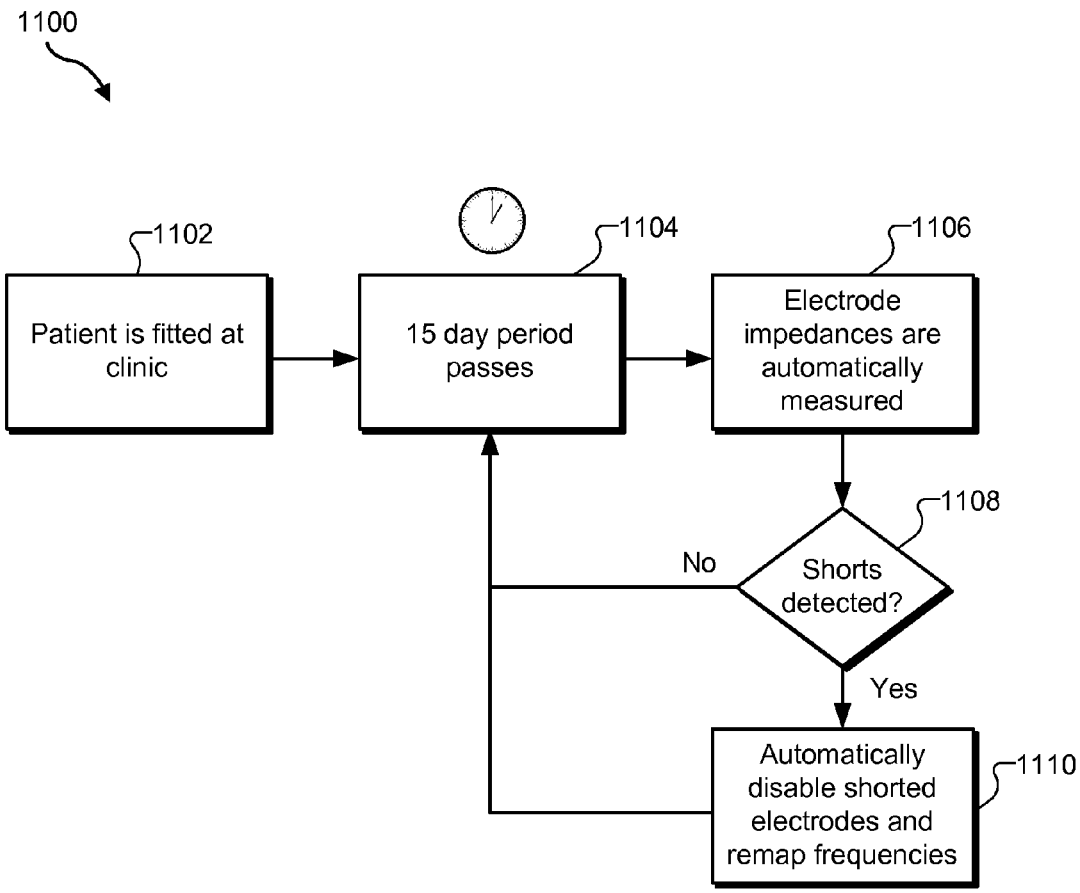

FIG. 10 illustrates another scenario 1000 in which a sound processor may be programmed to periodically perform EFI and NRI measurements. In step 1002, an auditory prosthesis patient is fitted at a clinic. During the fitting, the audiologist may program the sound processor to periodically (i.e., every 90 days) perform EFI and NRI measurements and adjust a sound processing program governing an operation of the sound processor accordingly. NRI measurements can take a relatively long amount of time to perform. Hence, it may be more practical space such measurements out over a longer period of time (e.g., every 90 days) in order to minimize disruption to the patient.

After the 90 day period passes (step 1004), the EFI and NRI measurements are automatically performed by the sound processor (steps 1006 and 1008). Based on the results of the EFI and NRI measurements, the sound processing program may be adjusted (step 1010). For example, one or more control parameters associated with the sound processing program may be modified. Once again, by automatically performing each of these fitting operations, numerous trips by the patient to the audiologist's clinic may be avoided.

FIG. 11 illustrates another scenario 1100 in which a sound processor may be programmed to periodically measure electrode impedances in order to detect one or more electrode shorts. During the fitting, the audiologist may program the sound processor to periodically (i.e., every 15 days) perform electrode impedance measurements in order to detect one or more electrode shorts. Electrode shorts may result in distorted sound as perceived by the patient. Hence, it may be desirable to perform such measurements relatively often (e.g., every 15 days).

After the 15 day period passes (step 1104), the electrode impedances are automatically measured by the sound processor (step 1108). Based on the results of these measurements, the sound processor may determine whether any of the electrodes are shorted. If one or more electrode shorts are detected (step 1108), the sound processor may automatically disable the shorted electrodes and remap their associated frequencies to other functioning electrodes (step 1110). If no shorts are detected, the sound processor does not have to take any remedial action.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 12:
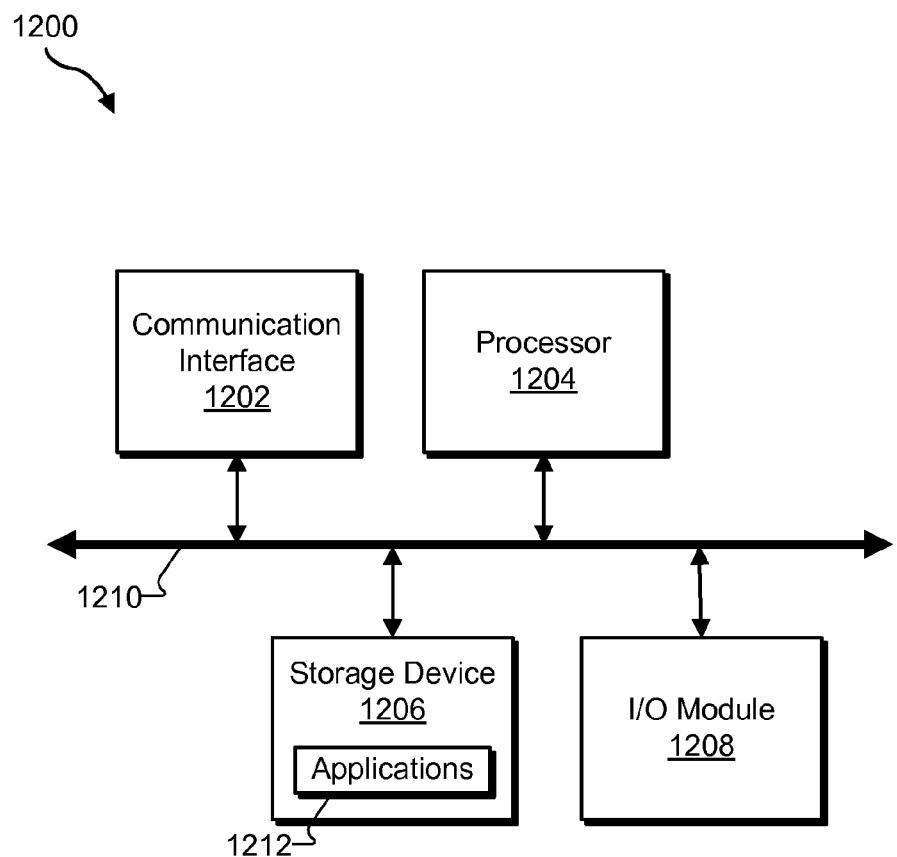
FIG. 12 illustrates an exemplary computing device according to principles described herein.

FIG. 12 illustrates an exemplary computing device 1200 that may be configured to perform one or more of the processes described herein. As shown in FIG. 12, computing device 1200 may include a communication interface 1202, a processor 1204, a storage device 1206, and an input/output ("I/O") module 1208 communicatively connected via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, and any other suitable interface. Communication interface 1202 may additionally or alternatively provide such a connection through, for example, a local area network (such as an Ethernet network), a personal area network, a telephone or cable network, a satellite data connection, a dedicated URL, or any other suitable connection. Communication interface 1202 may be configured to interface with any suitable communication media, protocols, and formats, including any of those mentioned above.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another non-transitory computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1206. For example, data representative of one or more executable applications 1212 (which may include, but are not limited to, one or more of the software applications described herein) configured to direct processor 1204 to perform any of the operations described herein may be stored within storage device 1206. In some examples, data may be arranged in one or more databases residing within storage device 1206.

I/O module 1208 may be configured to receive user input and provide user output and may include any hardware, firmware, software, or combination thereof supportive of input and output capabilities. For example, I/O module 1208 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1208 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1200. For example, one or more applications 1212 residing within storage device 1206 may be configured to direct processor 1204 to perform one or more processes or functions associated with communication facility 302, user interface facility 304, fitting facility 306, programming facility 308, communication facility 402, processing facility 404, clock facility 406, and/or fitting facility 408. Likewise, storage facility 310 and/or storage facility 410 may be implemented by or within storage device 1206.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow.

For example, certain features of one embodiment described herein may be combined with or substituted for features of another embodiment described herein. The description and drawings are accordingly to be regarded in an illustrative rather than a restrictive sense.

What is claimed is:

1. A sound processor included in an auditory prosthesis system and comprising:
    a clock facility that detects an elapsing of a predetermined amount of time; and
    a fitting facility communicatively coupled to the clock facility and that automatically performs, in response to the elapsing of the predetermined amount of time, one or more fitting operations with respect to the auditory prosthesis system by
        detecting one or more shorted electrodes included in a plurality of electrodes included in the auditory prosthesis system,
        disabling the one or more shorted electrodes, and
        remapping frequencies associated with the one or more shorted electrodes to one or more non-shorted electrodes included in the plurality of electrodes.

2. The sound processor of claim 1, wherein the fitting facility determines that the sound processor is operatively coupled to an auditory prosthesis included in the auditory prosthesis system before performing the one or more fitting operations.

3. The sound processor of claim 1, wherein the fitting facility is configured to interface with a fitting subsystem and receive programming instructions from the fitting subsystem that are representative of the predetermined amount of time and the one or more fitting operations that are to be performed in response to the elapsing of the predetermined amount of time.

4. The sound processor of claim 1, wherein:
    the clock facility detects an elapsing of an additional predetermined amount of time; and
    the fitting facility automatically directs, in response to the elapsing of the additional predetermined amount of time, the sound processor to switch from operating in accordance with a first sound processing program to operating in accordance with a second sound processing program.

5. The sound processor of claim 1, wherein:
    the clock facility detects an elapsing of an additional predetermined amount of time; and
    the fitting facility automatically performs, in response to the elapsing of the additional predetermined amount of time, one or more measurements associated with the auditory prosthesis system.

6. The sound processor of claim 5, wherein the fitting facility adjusts one or more control parameters associated with a sound processing program governing an operation of the sound processor in accordance with the one or more measurements.

7. The sound processor of claim 5, wherein the one or more measurements comprise at least one of an electrode impedance measurement, an electrical field imaging measurement, and a neural response imaging measurement.

8. The sound processor of claim 1, wherein:
    the clock facility detects subsequent elapsings of the predetermined amount of time;
    the fitting facility periodically performs the one or more fitting operations in accordance with the subsequent elapsings of the predetermined amount of time.

9. The sound processor of claim 1, wherein the clock facility is configured to operate while the sound processor is in an off state.

10. The sound processor of claim 1, wherein the clock facility is implemented by a counter.

11. The sound processor of claim 1, wherein the clock facility is implemented by a clock that tracks actual times and dates.

12. A system comprising:
a fitting facility that performs an initial fitting operation with respect to an auditory prosthesis system used by a patient while a sound processor included in the auditory prosthesis system is communicatively coupled to the system;
a user interface facility communicatively coupled to the fitting facility and that receives user input representative of an amount of time and a subsequent fitting operation to be performed by the sound processor with respect to the auditory prosthesis system in response to an elapsing of the amount of time, the subsequent fitting operation comprising
detecting one or more shorted electrodes included in a plurality of electrodes included in the auditory prosthesis system,
disabling the one or more shorted electrodes, and
remapping frequencies associated with the one or more shorted electrodes to one or more non-shorted electrodes included in the plurality of electrodes; and
a programming facility communicatively coupled to the user interface facility and that programs the sound processor to automatically perform the subsequent fitting operation in response to an elapsing of the amount of time.

13. The system of claim 12, wherein the initial fitting operation comprises directing the sound processor to operate in accordance with a first sound processing program and wherein the subsequent fitting operation further comprises directing the sound processor to operate in accordance with a second sound processing program.

14. The system of claim 12, wherein the elapsing of the amount of time occurs after the sound processor has been communicatively decoupled from the system.

15. A method comprising:
detecting, by a sound processor included in an auditory prosthesis system, an elapsing of a predetermined amount of time;
automatically performing, by the sound processor in response to the elapsing of the predetermined amount of time, one or more fitting operations with respect to the auditory prosthesis system by
detecting one or more shorted electrodes included in a plurality of electrodes included in the auditory prosthesis system,
disabling the one or more shorted electrodes, and
remapping frequencies associated with the one or more shorted electrodes to one or more non-shorted electrodes included in the plurality of electrodes.

16. The method of claim 15, further comprising receiving, by the sound processor, programming instructions from a fitting subsystem that are representative of the predetermined amount of time and the one or more fitting operations that are to be performed in response to the elapsing of the predetermined amount of time.

17. The method of claim 15, wherein the automatically performing further comprises switching from operating in accordance with a first sound processing program to operating in accordance with a second sound processing program.

18. The method of claim 15, wherein the automatically performing further comprises performing one or more measurements associated with the auditory prosthesis system.

19. The method of claim 15, embodied as computer-executable instructions on at least one non-transitory computer-readable medium.

* * * * *